US005779882A

United States Patent [19]
Chester et al.

[11] Patent Number: 5,779,882
[45] Date of Patent: Jul. 14, 1998

[54] MODIFIED MCM-56, ITS PREPARATION AND USE

[75] Inventors: Arthur W. Chester, Cherry Hill, N.J.; Anthony S. Fung, Wilmington, Del.; Charles T. Kresge, West Chester, Pa.; Wieslaw J. Roth, Sewell, N.J.

[73] Assignee: Mobil Oil Corporation, Fairfax, Va.

[21] Appl. No.: 684,673

[22] Filed: Jul. 22, 1996

[51] Int. Cl.[6] .............. C10G 11/05; C07C 2/58; C07C 2/66; B01J 29/06

[52] U.S. Cl. .......... 208/120; 585/467; 585/722; 502/67; 502/79; 502/85; 423/717; 423/718

[58] Field of Search .............. 585/467, 722; 208/120; 502/67, 79, 85; 423/717, 718

[56] References Cited

U.S. PATENT DOCUMENTS

| | | | |
|---|---|---|---|
| 5,234,872 | 8/1993 | Apelian et al. | 502/62 |
| 5,284,989 | 2/1994 | Apelian et al. | 585/533 |
| 5,308,471 | 5/1994 | Apelian et al. | 208/89 |
| 5,362,697 | 11/1994 | Fung et al. | 502/71 |
| 5,453,554 | 9/1995 | Cheng et al. | 585/467 |
| 5,536,894 | 7/1996 | Degnan et al. | 585/467 |
| 5,552,357 | 9/1996 | Lago et al. | 502/63 |
| 5,557,024 | 9/1996 | Cheng et al. | 585/467 |

*Primary Examiner*—Walter D. Griffin
*Attorney, Agent, or Firm*—Peter W. Roberts; Ronald J. Cier

[57] ABSTRACT

A layered composition of matter, MCM-56, has an X-ray diffraction pattern including lines at d-spacing values of 12.4±0.2, 9.9±0.3, 6.9±0.1, 6.2±0.1, 3.55±0.07 and 3.42±0.07 Angstroms and has been selectively modified so that the ratio of the number of active acid sites at its external surface to the number of internal active acid sites is greater than that of the unmodified material. When used as an additive to a large pore zeolite catalyst in the catalytic cracking of a petroleum feedstock, the modified MCM-56 gives an improved gasoline yield/octane relationship, an improved coke selectivity and a higher combined gasoline and potential alkylate yield than an identical catalyst containing unmodified MCM-56.

20 Claims, No Drawings

MODIFIED MCM-56, ITS PREPARATION AND USE

BACKGROUND OF THE INVENTION

1. Field of the Invention

This invention relates to selectively modified MCM-56, to a method of its preparation and to its use as a sorbent and a catalyst component for conversion of organic compounds, in particular as a component of a catalytic cracking catalyst.

2. Description of the Prior Art

MCM-56 is a porous inorganic solid and is described in U.S. Pat. No. 5,362,697, the entire contents of which are incorporated herein by reference.

Porous inorganic solids have found utility as catalysts and separation media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the detail in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100–250 Angstrom particles of dense amorphous silica (*Kirk-Othmer Encyclopedia of Chemical Technology*, 3rd Edition, Vol. 20, John Wiley & Sons, New York, p. 766–781, 1982), with the porosity resulting from voids between the particles. Since there is no long range order in these materials, the pores tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum", Technical Paper No. 19 Revised, Alcoa Research Laboratories, p. 54–59, 1987). Since, in the case of either material, there is no long range order controlling the sizes of pores in the material, the variability in pore size is typically quite high. The sizes of pores in these materials fall into a regime called the mesoporous range, including, for example, pores within the range of about 15 to about 200 Angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g., $AlO_4$, in which the tetrahedra are cross-linked by the sharing of oxygen atoms whereby the ratio of the total Group IIIB element, e.g., aluminum, and Group IVB element, e.g., silicon, atoms to oxygen atoms is 1:2. The electrovalence of the tetrahedra containing the Group IIIB element, e.g., aluminum, is balanced by the inclusion in the crystal of a cation, for example, an alkali metal or an alkaline earth metal cation. This can be expressed wherein the ratio of the Group IIIB element, e.g., aluminum, to the number of various cations, such as $Ca/2$, $Sr/2$, $Na$, $K$ or $Li$, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolites A (U.S. Pat. No. 2,882, 243); X (U.S. Pat. No. 2,882,244); Y (U.S. Pat. No. 3,130, 007); ZK-5 (U.S. Pat. No. 3,247,195); ZK-4 (U.S. Pat. No. 3,314,752); ZSM-5 (U.S. Pat. No. 3,702,886); ZSM-11 (U.S. Pat. No. 3,709,979); ZSM-12 (U.S. Pat. No. 3,832, 449), ZSM-20 (U.S. Pat. No. 3,972,983); ZSM-35 (U.S. Pat. No. 4,016,245); ZSM-23 (U.S. Pat. No. 4,076,842); MCM-22 (U.S. Pat. No. 4,954,325); MCM-35 (U.S. Pat. No. 4,981,663); MCM-49 (U.S. Pat. No. 5,236,575); and PSH-3 (U.S. Pat. No. 4,439,409).

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, trititanates and perovskites. Another example of a non-water swellable layered material, which can be swollen with certain organic swelling agents, is a vacancy-containing titanometallate material, as described in U.S. Pat. No. 4,831,006.

Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090; and 4,367,163; and European Patent Application No. 205,711.

The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle region on the X-ray diffraction pattern is observed, at a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

MCM-56 (and the related MCM-22) is an unusual material in that it exhibits features of both layered and zeolitic materials. Thus MCM-56 has layers which are microporous and contain cation-exchangeable acid sites. This leads to the presence of acid sites at two different locations; acid sites are located on the large external surface of MCM-56 and further acid sites are located within the internal pore structure of the layers. These further internal acid sites are only accessible through the pore openings in the layers which are believed to be elliptical with dimensions of about 5.9 by 4.0 Angstrom.

SUMMARY OF THE INVENTION

According to the present invention, it has now been found that the catalytic and sorptive properties of MCM-56 can be significantly altered by selectively modifying the material so that the ratio of the number of active acid sites at its external surface to the number of internal active acid sites is different, and preferably greater, than that of unmodified MCM-56. For example, MCM-56 modified so as to selectively increase the ratio of its external to internal acid activity has been found to result in an unexpected increase in the yield of high value liquid products, such as gasoline and distillate, and less bottoms fraction and coke, as compared to unmodified MCM-56, when used as an additive to a conventional zeolite Y cracking catalyst.

In one aspect, therefore, the present invention resides in a layered composition of matter, MCM-56, which has an X-ray diffraction including the lines listed in Table II below and which has been selectively modified so that the ratio of the number of active acid sites at its external surface to the number of internal active acid sites is greater than that of the unmodified material.

DESCRIPTION OF SPECIFIC EMBODIMENTS

The layered MCM-56 material of the invention has an X-ray diffraction pattern which is distinguished by the combination of line positions and intensities from the patterns of other known as-synthesized or thermally treated materials as shown below in Table I (as synthesized) and Table II (calcined). In these tables, intensities are defined relative to the d-spacing line at 12.4 Angstroms.

TABLE I

MCM-56 (as-synthesized)

| Interplanar d-spacing (A) | Relative Intensity |
|---|---|
| 12.4 ± 0.2 | vs |
| 9.9 ± 0.3 | m |
| 6.9 ± 0.1 | w |
| 6.4 ± 0.3 | w |
| 6.2 ± 0.1 | w |
| 3.57 ± 0.07 | m–s |
| 3.44 ± 0.07 | vs |

TABLE II

MCM-56 (as-calcined)

| Interplanar d-Spacing (A) | Relative Intensity |
|---|---|
| 12.4 ± 0.2 | vs |
| 9.9 ± 0.3 | m–s |
| 6.9 ± 0.1 | w |
| 6.2 ± 0.1 | s |
| 3.55 ± 0.07 | m–s |
| 3.42 ± 0.07 | vs |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

The layered material MCM-56 of this invention has a composition involving the molar relationship:

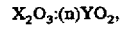

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 35, e.g. from about 5 to less than about 25, usually from about 10 to less than about 20, more usually from about 13 to about 18. In the as-synthesized form, the material has a formula, on an anhydrous basis and in terms of moles of oxides per n moles of $YO_2$, as follows:

$$(0-2)M_2O:(1-2)R:X_2O_3:(n)YO_2$$

wherein M is an alkali or alkaline earth metal, and R is an organic moiety. The M and R components are associated with the material as a result of their presence during synthesis, and are easily removed by post-synthesis methods hereinafter more particularly described.

To the extent desired, the original alkali or alkaline earth, e.g. sodium, cations of the as-synthesized MCM-56 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the calcined form, MCM-56 exhibits high surface area (greater than 300 m²/gm) and unusually large sorption capacity for certain large molecules when compared to previously described materials such as calcined PSH-3, SSZ-25, MCM-22, and MCM-49. Thus calcined MCM-56 is characterised by a sorption capacity for 1,3,5-trimethylbutane of at least about 35 µl/gram and an initial uptake of 2,2-dimethylbutane of 15 mg/gram in less than about 20 seconds.

MCM-56 can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, said reaction mixture having a composition, in terms of mole ratios of oxides, within the following ranges:

| Reactants | Useful | Preferred |
|---|---|---|
| $YO_2/X_2O_3$ | 5 to 35 | 10 to 25 |
| $H_2O/YO_2$ | 10 to 70 | 16 to 40 |
| $OH^-/YO_2$ | 0.05 to 0.5 | 0.06 to 0.3 |
| $M/YO_2$ | 0.05 to 3.0 | 0.06 to 1.0 |
| $R/YO_2$ | 0.1 to 1.0 | 0.3 to 0.5 |

The source of $YO_2$ should comprise predominantly solid $YO_2$, for example at least about 30 wt. % solid $YO_2$ in order to obtain the crystal product of the invention. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-56 formation from the above mixture under the synthesis conditions required. Preferably, therefore, the $YO_2$, e.g. silica, source contains at least about 30 wt. % solid $YO_2$, e.g. silica, and more preferably at least about 40 wt. % solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof, with hexamethyleneimine being particularly preferred.

Crystallization of the present layered material can be carried out under either static or stirred conditions in a suitable reactor vessel, such as for example polypropylene jars or teflon lined or stainless steel autoclaves, at a temperature of about 80° C. to about 225° C. It is critical, however, in the synthesis of MCM-56 from the above reaction mixture to stop and quench the reaction prior to the onset of MCM-49 formation at the expense of MCM-56. One method for controlling the synthesis to produce the required MCM-56 is disclosed in U.S. Pat. No. 5,362,697 and involves monitoring the X-ray diffraction pattern in the 8.8–11.2 Angstrom d-spacing range. MCM-56 is characterized by a broad band centered around d-spacing 9.9 Angstroms, whereas MCM-49 exhibits two resolved maxima at approximately 8.8–9.2 Angstroms and 10.8–11.2 Angstroms with a distinct depression between them. While the band in the 8.8–11.2 Angstrom d-spacing range for the synthesis mixture may have an asymmetric profile, for example with an inflection point, the emergence of a depression may be indicative of the onset of MCM-49 formation and the loss of MCM-56.

It should be realized that the reaction mixture components can be supplied by more than one source. The reaction mixture can be prepared either batchwise or continuously.

After synthesis is complete, the MCM-56 is separated from the reaction mixture and is then conveniently dehydrated and treated to remove the organic directing agent.

Dehydration is generally performed by heating to a temperature in the range of 200° C. to about 370° C. in an atmosphere such as air, nitrogen, etc. and at atmospheric, subatmospheric or superatmospheric pressures for between 30 minutes and 48 hours. Dehydration can also be performed at room temperature merely by placing the MCM-56 in a vacuum, but a longer time is required to obtain a sufficient amount of dehydration.

Removal of the organic directing agent is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C.

The resultant MCM-56 is subjected to the selective modification procedure of the invention so as to alter the ratio of the surface acid activity of the material to its internal acid activity.

One suitable method for selective modification involves a multi-stage ion exchange procedure, in which the calcined MCM-56 is initially contacted with a catalytically inactive cation, which is capable of occupying all the exchange sites, both internal and external, of the MCM-56. Suitable cations have dimensions less than the pore windows of MCM-56, which have dimensions of 5.9×4 Angstrom, and include the sodium cation, the potassium cation and the cesium cation. The product is then back-exchanged with a bulky cation which replaces the cations on the external surface of the MCM-56 but which, by virtue of its size, is sterically hindered from entering the pore openings of the material. Suitable bulky cations have at least one dimension greater than 6 Angstrom and include the tetrapropylammonium ($TPA^+$) cation, the tetraethylammonium ($TEA^+$) cation and the tetrabutylammonium ($TBA^+$) cation.

Another suitable method for-selective modification involves coating the external surface of the MCM-56 with a catalytically active or inactive material, such as alumina or silica, so as to increase or decrease respectively the surface activity compared to the internal activity of the MCM-56.

A convenient method of measuring the surface acidity of MCM-56, exclusive of its internal acidity, is to determine its activity for the dealkylation of 1,3,5-tri-tertbutylbenzene (TTBB), a bulky molecule that can only react with the acid sites on the surface of the material.

Dealkylation of TTBB is a facile, reproducible method for measuring surface acidity of catalysts. External surface activity can be measured exclusive of internal activity for zeolites with pore diameters up to and including faujasite. As a test reaction dealkylation of TTBB occurs at a constant temperature in the range of from about 25° to about 300° C., and preferably in the range of from about 200° to about 260° C.

The experimental conditions for the test used herein include a temperature of 200° C. and atmospheric pressure. The dealkylation of TTBB is carried out in a glass reactor (18 cm×1 cm OD) containing an 8 gm 14/30 mesh Vycor chip preheater followed by 0.1 gm catalyst powder mixed with Vycor chips. The reactor is heated to 200° C. in 30 cc/gm nitrogen for 30 minutes to remove impurities from the catalyst sample. Ten gm/hr of TTBB dissolved in toluene (7% TTBB) is injected into the reactor. The feed vaporizes as it passes through the preheater and is vapor when passing over the catalyst sample. After equilibrium is reached the nitrogen is switched to 20 cc/min hydrogen. The test is then run for about 30 minutes and the reaction products are analyzed by gas chromatography.

The major dealkylation product is di-t-butylbenzene (DTBB). Further dealkylation to t-butylbenzene (TBB) and benzene (B) occurs but to a lesser extent. Conversion of TTBB is calculated on a molar carbon basis. Dealkylation product weight % are each multiplied by the appropriate carbon number ratio to convert to the equivalent amount of TTBB, i.e. DTBB×18/14, TBB×18/10 and B×18/6. These values are then used in the following conversion equation where asterisks indicate adjustment to the equivalence.

$$\% \ TTBB \ \text{Conversion} = \frac{DTBB^* + TBB^* + B^*}{TTBB + DTBB^* + TBB^* + B^*}$$

The coefficient of reaction, $k_{TTBB}$ is then calculated on the assumption that that the conversion of TTBB is a first order reaction according to the equation:

$$k_{TTBB} = \frac{\text{Gas flow rate, cc/min} \times \ln(1 - \epsilon_{TTBB})}{60 \times \text{Catalyst volume, cc}}$$

where $\epsilon_{TTBB}$ is the fractional conversion of TTBB at 30 minutes on stream.

In the case of MCM-56, the TTBB conversion is accompanied by significant conversion of toluene by disproportionation into benzene and xylenes. The toluene conversion is calculated based on the weight % of toluene in the feed converted and, again assuming that the conversion is a first order reaction, $k_{Toluene}$ is derived from:

$$k_{Toluene} = \frac{\text{Gas flow rate, cc/min} \times \ln(1 - \epsilon_{Toluene})}{60 \times \text{Catalyst volume, cc}}$$

where $\epsilon_{Toluene}$ is the fractional conversion of toluene at 30 minutes on stream.

A convenient method of measuring the overall acidity of MCM-56, inclusive of both its internal and external acidity, is the alpha test, which is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

Thus the selective modification of the invention can be demonstrated by comparing the TTBB conversion and the alpha value of the MCM-56 before and after modification.

The modified MCM-56 material of this invention may be used as an adsorbent, such as for separating at least one component from a mixture of components in the vapor or liquid phase having differential sorption characteristics with respect to MCM-56. Therefore, at least one component can be partially or substantially totally separated from a mixture of components having differential sorption characteristics with respect to MCM-56 by contacting the mixture with the MCM-56 to selectively sorb the one component.

The modified MCM-56 material of this invention can also be used to catalyze a wide variety of chemical conversion processes including many of present commercial/industrial importance. When used as a catalyst, the modified MCM-56 material of the invention may be intimately combined with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

When used as a catalyst, it may be desirable to incorporate the modified MCM-56 of the invention with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the MCM-56, i.e. combined therewith or present during synthesis of MCM-56, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present MCM-56 layered material also include inorganic oxides, notably alumina.

In addition to the foregoing materials, the MCM-56 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided MCM-56 material and inorganic oxide matrix vary widely, with the MCM-56 content ranging from about 1 to about 90 percent by weight and more usually, particularly when the composite is prepared in the form of beads, in the range of about 2 to about 80 weight percent of the composite.

The modified MCM-56 produced according to the invention is particularly intended for use as an additive catalyst to a catalytic cracking catalyst. Conventional cracking catalysts comprise a primary cracking component, which may be amorphous, such as silica/alumina, but more normally comprises a large pore crystalline zeolite, such as zeolite X, zeolite Y, REY or US-REY, ZSM-20 or zeolite L. In addition, to the large pore zeolite, such as zeolite Y, conventional cracking catalysts contain other components, notably a matrix for the zeolite. When a matrix is used, the content of the large pore zeolite is conveniently about 5 to 50% by weight of the matrixed catalyst.

The modified MCM-56 according to the invention can be added to such a conventional cracking catalyst, either as a separate particle, typically bound with a separate matrix, or combined with the large pore zeolite as a single particle. The amount of modified MCM-56 present in the cracking catalyst can vary between 0.5% and 90% by weight, and preferably is between 2% and 45% by weight, of the overall cracking catalyst.

Cracking catalysts containing the modified MCM-56 of the invention are useful in both fluid catalytic cracking (FCC) and Thermofor catalytic cracking (TCC). Such processes typically operate at temperatures between 200° C. and 700° C. and under reduced or superatmospheric pressure.

Catalysts containing the modified MCM-56 of the invention can be used to crack a wide variety of heavy hydrocarbon feedstocks, such as petroleum fractions having an initial boiling point of 200° C., a 50% point of at least 260° C. and an end point in excess of 315° C. Such hydrocarbon feedstocks include gas oils, residual oils, cycle stocks, whole and topped crudes and the heavy hydrocarbon fractions derived from the destructive hydrogenation of coal, tar, pitches asphalts and the like.

According to the invention, it has surprisingly been found that cracking of a petroleum feedstock with a catalyst MCM-56 which has been modified to increase the ratio of external activity to internal activity gives an improved gasoline yield/octane relationship, an improved coke selectivity and a higher combined gasoline and potential alkylate yield than an identical catalyst containing unmodified MCM-56.

Examples of other chemical conversion processes which are effectively catalyzed by the modified MCM-56 of the invention, by itself or in combination with one or more other catalytically active substances including other crystalline catalysts, include:

(1) alkylation of aromatic hydrocarbons, e.g. benzene, with long chain olefins, e.g. $C_{14}$ olefin, with reaction conditions including a temperature of from about 340° C. to about 500° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(2) alkylation of aromatic hydrocarbons with gaseous olefins to provide short chain alkyl aromatic compounds, e.g. the alkylation of benzene with propylene to provide cumene, with reaction conditions including a temperature of from about 10° C. to about 125° C., a pressure of from about 1 to about 30 atmospheres, and an aromatic hydrocarbon weight hourly space velocity (WHSV) of from 5 $hr^{-1}$ to about 50 $hr^{-1}$;

(3) alkylation of reformate containing substantial quantities of benzene and toluene with fuel gas containing $C_5$ olefins to provide, inter alia, mono- and dialkylates with reaction conditions including a temperature of from about 315° C. to about 455° C., a pressure of from about 400 to about 800 psig, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(4) alkylation of aromatic hydrocarbons, e.g., benzene, toluene, xylene and naphthalene, with long chain olefins, e.g. $C_{14}$ olefin, to provide alkylated aromatic lube base stocks with reaction conditions including a temperature of from about 160° C. to about 260° C. and a pressure of from about 350 to 450 psig;

(5) alkylation of phenols with olefins or equivalent alcohols to provide long chain alkyl phenols with reaction conditions including a temperature of from about 200° C. to about 250° C., a pressure of from about 200 to 300 psig and a total WHSV of from about 2 $hr^{-1}$ to about 10 $hr^{-1}$; and (6) alkylation of isoalkanes, e.g. isobutane, with olefins, e.g. 2-butene, with reaction conditions including a temperature of from about −25° C. to about 400° C., e.g., from 75° C. to 200° C., a pressure of from below atmospheric to about 35000 kPa.(5000 psig), e.g. from 100 to 7000 kPa (1 to 1000 psig), a weight hourly space velocity based on olefin of from about 0.01 $hr^{-1}$ to about 100 $hr^{-1}$, e.g. from 0.1 $hr^{-1}$ to 20 $hr^{-1}$, and a mole ratio of total isoalkane to total olefin of from about 1:2 to about 100:1, e.g. from 3:1 to 30:1.

In order to more fully illustrate the nature of the invention and the manner of practicing same, the following examples are presented.

EXAMPLE 1

This example demonstrates the preparation of the hydrogen form of MCM-56.

A sample of as-synthesized MCM-56 prepared as described in U.S. Pat. No. 5,362,697 was ammonium exchanged and was dried at 250° F. (120° C.) overnight. The dried ammonium exchanged MCM-56 was first heated in flowing nitrogen at 900° F. (480° C.) for 3 hours to decompose the directing agent followed by calcining in flowing air at 1000° F. (540° C.) for 6 hours. The resulting MCM-56 sample was in the [H]-form and was designated as sample A. The properties of sample A are listed in Table III below.

EXAMPLE 2

This example discloses the preparation of selective cation exchanged MCM-56.

529 g of sample A from Example 1 was slurried in 2650 ml of a 1N NaCl solution for 2 hours. The sample was filtered and washed with deionized water. The filter cake was re-slurried in 2650 ml of 1N NaCl solution for 2 hours, and was filtered and washed. The filtercake was dried at 250° F. overnight. The dried MCM-56 sample was in the [Na]-form and was designated as sample B. The properties of sample B are listed in Table III below.

600 g of sample B was slurried in 6 liter of 35% tetrapropylammonium bromide ([TPA]Br) solution for 2 hours. The sample was filtered and washed with deionized water until no residual bromide was detected in the filtrate. The filtercake was re-slurried in another 6 liter of 35% tetrapropylammonium bromide solution for another 2 hours. After filtering and washing with deionized water, the filtered cake was dried at 250° F. (120° C.) overnight. The dried MCM-56 sample was in the [TPA]/[Na]-form and was designated as sample C. The properties of sample C are listed in Table III below.

The selective ion exchange process described above involved the use of a small cation, sodium [Na]$^+$, to occupy all exchange (acid) sites in MCM-56. The sodium cations on the sample were then back exchanged with a bulky cation, tetrapropylammonium, [TPA]$^+$. Due to the bulky dimension of [TPA]$^+$ cation, it was selectively exchanged with the sodium cations located on the external surface of MCM-56. For those exchange (acid) sites located within the layer, they remained occupied with sodium because the [TPA]$^+$ cations were too large to access through the 10-ring pore openings of MCM-56 during the second exchange.

EXAMPLE 3

This example discloses the preparation of "alumina-coated" MCM-56.

A 1852 g of sample A from Example 1 was slurried in 9 liters of 1N ammonium nitrate solution for 1 hour. The slurry was filtered and washed with deionized water. The filter cake was dried at 250° F. (120° C.) overnight.

An alum solution was prepared by adding 112.5 g of deionized water to 1406 g of aluminum sulfate (8 wt. % Al$_2$O$_3$) solution. The density of the diluted alum solution is 1.38 g/ml. A sodium aluminate solution was prepared by adding 886 g of sodium aluminate (USALCO 45) to 39.8 g of caustic soda. The density of the sodium aluminate solution is 1.54 g/ml. A second sodium aluminate solution was also prepared using the same procedure.

The dried filtercake (845 g) was first slurried in deionized water, and the slurry was heated up to 120° F. (50° C.). After the temperature of the slurry equilibrated at 120° F. (50° C.), the alum solution and the first sodium aluminate solution were introduced to the slurry simultaneously by using two separate pumps. The pH of the slurry was maintained at pH 7.4–7.6 by adjusting the flow rate of the sodium aluminate solution. After completing the addition of the two solutions, the slurry was allowed to stir at 120° F. (50° C.) for an additional 10 minutes. The second sodium aluminate solution was then introduced to the slurry. The final pH of the slurry was allowed to stabilize at 9.8–10.0 at 120° F. (50° C.). The slurry was stirred at 120° F. (50° C.) for an additional 30 minutes, and was filtered and washed with hot deionized water. The filtercake was further washed with deionized water until the pH of the filtrate was below 9. The filtercake was dried at 250° F. (120° C.) overnight. The dried filter cake was ammonium exchanged and was calcined at 1000° F. (540° C.) for 3 hours. The calcined sample was the "alumina-coated" MCM-56 and was designated as sample D.

The properties of sample D are listed in Table III below.

TABLE III

| | Sample I.D. | | | |
|---|---|---|---|---|
| | A | B | C | D |
| Example | 1 | 2 | 2 | 3 |
| Form | [H] | [Na] | [TPA]/[Na] | Alumina-coated |
| SiO$_2$, wt % | 84.8 | 82 | 70 | 49.2 |
| Al$_2$O$_3$, wt % | 8 | 9 | 6 | 39 |
| Na, wt % | 0.038 | 4.63 | 0.926 | 0.041 |
| N, wt % | — | — | 1.2 | — |
| Ash, % | 94.5 | 88.5 | 79.5 | 96 |
| Alpha* | 121 | 0.7 | 39 | 94 |
| TTBB Test | | | | |
| K$_{TTBB}$, s$^{-1}$ | 0.24 | 0.0 | 3.07 | 5.02 |
| K$_{toluene}$, s$^{-1}$ | 0.95 | N/a | 0.08 | 0.06 |
| n-C$_6$, wt % (@90° C.) | 5.03 | 3.49 | 4.89 | 2.57 |
| Na/Al (atomic ratio) | 0.01 | 1.14 | 0.27 | <0.01 |
| (Na + N)/Al (atomic ratio) | — | — | 1.0 | — |

*The alpha measurements were conducted on the samples after calcination at 1000° F. (540° C.). For sample C, it was first calcined in nitrogen at 900° F. (480° C.) to decompose the [TPA]$^+$ cations followed by air calcining at 1000° F. (540° C.).

Table III shows that after sodium exchange, all exchange sites in MCM-56 (Sample B) were occupied by sodium cations, as indicated by a Na/Al ratio of 1.14. After the [TPA]Br exchange (Sample C), approximately 73% of the exchange sites were not occupied by sodium cations, as indicated by a Na/Al ratio of 0.27. The results of the alpha measurements were also consistent with the elemental analyses. As all the exchange (acid) sites were occupied with sodium cations, sample B exhibited insignificant alpha cracking activity. In contrast, sample C demonstrated an alpha value of 39, consistent with only part of the exchange (acid) sites still being occupied by sodium cations. For sample D, although the alpha value was only 94 (less than the alpha value of sample A), comparison of the n-C$_6$ uptake at 90° C. of samples A and D indicates that the MCM-56 content of sample D was only about 51% by weight.

Table III also shows that the catalytic properties of sample A were dominated by the conversion of toluene which mostly occurred at the internal acid sites. The conversion of TTBB with sample A was an order of magnitude smaller than those of sample C and D. The conversion of TTBB in the presence of toluene demonstrated the unique catalytic properties of the modified MCM-56 of samples C and D. Both samples C and D showed a high TTBB conversion but with a minimum conversion of toluene, which is consistent with the internal acid sites being blocked by sodium or with the accessability to the internal acid sites being limited by the alumina coating. Sample B exhibited no conversion of TTBB or toluene since all acid sites were occupied by sodium.

EXAMPLE 4

This example demonstrates the preparation of rare earth exchanged USY.

A commercial USY, Z14US (Grace Davison), was ammonium exchanged. 4300 g of dried ammonium exchanged USY was slurried in 10.8 liter of deionized water. A rare earth chloride solution containing 844 g of RECl$_3$.7H$_2$O was added to the USY slurry. After completing the addition of the rare earth chloride solution, the slurry was stirred under ambient conditions overnight. The slurry was filtered and the filtercake was washed with deionized water until no chloride was detected in the filtrate. The filter cake was dried at 250° F. (120° C.) overnight and calcined at 1000° F. (540° C.)for 3 hours. This calcined sample was designated as sample E. Elemental analyses of sample E are listed below:

| | |
|---|---|
| $RE_2O_3$, wt % | 5.73 |
| Na, wt % | 0.489 |
| $Al_2O_3$, wt % | 22.1 |
| $SiO_2$, wt % | 65.5 |
| Unit cell size Å | 24.595 |
| Ash, % | 96.5 |

EXAMPLE 5

Three catalysts, designated catalysts G, H and I, were formulated with 20% rare earth exchanged USY (sample E) and 20% unmodified or modified MCM-56 using samples A, C, and D respectively in a 25% silica/35% clay matrix according to the following procedure.

932 g of ball milled rare earth exchanged USY slurry (32.2% solid) was introduced to 1103 g of colloidal silica (Nalco 1034A). The zeolite-silica slurry was mixed for at least 3 minutes. A 1282 g of ball milled modified or unmodified MCM-56 slurry (23.4% solid) was added to the zeolite-silica mixture and mixed for at least 3 minutes. 875 g of kaolin clay (Thiele RC-32) was then added to the mixture. Additional deionized water was added for satisfactory operation of the spray dryer. The pH of the slurry was maintained at pH 3.5–3.75.

The slurry was spray dried in a Bowen Engineering 2' diameter spray dryer with an outlet temperature of 350° F. (180° C.). The collected fluid catalyst was washed with deionized water and filtered. The wet cake was dried at 250° F. (120° C.) overnight. The dried product was first calcined in air at 1000° F. (540° C.) for 2 hours followed by steam deacitvation at 1450° F. (790° C.) in 45% steam/55% air, 0 psig (100 kPa) for 10 hours before catalytic testing. Table IV lists the properties of catalysts G, H and I.

EXAMPLE 6

A further catalyst, designated catalyst F, was formulated with 20% rare earth exchanged USY (sample E) in a 25% silica-55% clay matrix according to the following procedure:

932 g of ball milled rare earth exchanged USY slurry (32.2% solid) was introduced to 1103 g of colloidal silica (Nalco 1034A). The zeolite-silica slurry was mixed for at least 3 minutes. 1323 g of kaolin clay (Thiele RC-32) was then added to the mixture. Additional deionized water was added for satisfactory operation of the spray dryer. The pH of the slurry was maintained at pH 3.5–3.75.

The slurry was spray dried in a Bowen Engineering 2' diameter spray dryer with an outlet temperature of 350° F. (180° C.). The collected fluid catalyst was washed with deionized water and filtered. The wet cake was dried at 250° F. (120° C.) overnight. The dried product was first calcined in air at 1000° F. (540° C.) for 2 hours followed by steam deacitvation at 1450° F. (790° C.) in 45% steam/55% air, 0 psig (100 kPa) for 10 hours before catalytic testing. Table IV lists the properties of catalyst F.

TABLE IV

| Formulation | Catalyst | | | |
|---|---|---|---|---|
| | F | G | H | I |
| *RE-USY, wt % | 20 | 20 | 20 | 20 |
| MCM-56 sample type | None | Sample A | Sample C | Sample D |
| Clay matrix, wt % | 55 | 35 | 35 | 35 |
| Silica matrix, wt % | 25 | 25 | 25 | 25 |
| $SiO_2$, wt % | 65.2 | 73.3 | 72.1 | 66.4 |
| $Al_2O_3$, wt % | 28.3 | 21.3 | 21.3 | 27.5 |
| Na, wt % | 0.10 | 0.12 | 0.32 | 0.11 |
| $RE_2O_3$, wt % | 1.2 | 0.98 | 1.10 | 1.05 |
| Clay, wt % | 55 | 35 | 35 | 35 |
| Silica, wt % | 25 | 25 | 25 | 25 |
| Surface area, $m^2/g$ | 134 | 185 | 197 | 163 |
| Ash, % | 98.6 | 99.4 | 98.0 | 99.2 |

The results of the rare earth analyses on the four catalysts suggest that they have similar RE-USY content in each of the catalyst prepared. The results of the surface area measurements of the four steamed catalysts are consistent with the relative amount of MCM-56 in each of the catalyst.

EXAMPLE 7

Each of the catalysts F, G, H, and I was evaluated in a fixed fluidized bed reactor using a Joliet sour heavy gas oil (JSHGO) as a petroleum feedstock. The properties of the feedstock are listed in Table V below:

TABLE V

| Feed | JHSGO |
|---|---|
| API gravity | 19.7 |
| Pour Point, °F. (°C.) | 95 (35) |
| Kinematic Viscosity at 100 C., cs | 7.95 |
| Molecular weight | 369 |
| CCR, wt % | 0.56 |
| Aromatics, wt % | 55.3 |
| Saturates, wt % | 44.7 |
| Sulfur, wt % | 2.6 |
| Total nitrogen, ppm | 1500 |
| Basic nitrogen, ppm | 490 |
| Ni, ppm | 0.48 |
| V, ppm | 0.29 |
| Fe, ppm | 1.2 |
| Initial boiling point, °F. (°C.) | 497 (258) |
| 50% point, °F. (°C.) | 826 (441) |
| 90% point, °F. (°C.) | 1001 (583) |

The reactor temperature was 960° F. (515° C.), and the oil delivery time was 1 minute. At a cat-to-oil ratio of 4, the activity ranking based on the volume percent conversion of fresh feed was as follows:

H<G=I<F 75<73.2=73.5<71.1

Comparing the activity of catalyst F with those of catalyst G, H, and I, the presence of unmodified or modified MCM-56 helped to increase the conversion of a RE-USY containing catalyst. It is also surprising to note that catalyst H was the most active among the four catalysts as part of the acid sites on MCM-56 were occupied by sodium (ref. Sample C, Example 2). The similar conversions observed for catalyst G and I suggest that the alumina coating on MCM-56 enhanced its activity, as there was only approximately ~50% MCM-56 in the alumina-coated MCM-56 sample (ref. Sample D, Example 3).

The yield pattern of catalysts F, G, H, and I at 70 vol. % conversion is given in Table VI below:

TABLE VI

| | Catalyst | | | |
|---|---|---|---|---|
| | F | G | K | I |
| Light gas, wt % | 3.0 | 2.9 | 2.8 | 2.9 |
| $H_2$, wt % | 0.14 | 0.10 | 0.06 | 0.12 |
| Total $C_3$, vol. % | 7.9 | 11.1 | 9.6 | 9.4 |
| $C_3=/C_3$, mol/mol | 2.3 | 3.0 | 3.2 | 3.3 |
| Total $C_4$, vol. % | 13.7 | 18.0 | 15.1 | 16.1 |
| $C_4=/C_4$, mol/mol | 0.7 | 0.8 | 0.7 | 0.8 |
| $C_5^+$ Gasoline, vol % | 55.6 | 50.6 | 55.2 | 54.2 |
| $C_5^+$ Gasoline, wt % | 45.1 | 41.0 | 45.2 | 44.0 |
| LCO, wt % (430–740° F.) | 26.4 | 26.7 | 26.4 | 26.6 |
| HFO, wt % (740+° F.) | 6.3 | 6.2 | 6.3 | 6.2 |
| Coke, wt % | 6.2 | 5.7 | 4.5 | 5.0 |
| RON, $C_5^+$ Gasoline | 88.5 | 91.0 | 89.0 | 90.1 |
| Isobutane/($C_3 + C_4$) Olefins | 0.60 | 0.54 | 0.54 | 0.49 |
| Iso-$C_4=/C_4=$ | 0.19 | 0.29 | 0.27 | 0.26 |
| (Gasoline + LCO)/(HFO + Coke) | 5.7 | 5.7 | 6.6 | 6.3 |
| Potential alkylate, % vol. | 18.3 | 26.7 | 22.8 | 24.4 |
| Gasoline + Potential alkylate, % vol. | 73.9 | 77.3 | 77.9 | 78.6 |
| ΔRON/ΔGasoline loss (vol %) | Base | 0.5 | 1.3 | 1.1 |

The incorporation of unmodified or modified MCM-56 into a RE-USY containing catalyst improved the coke selectivity, the octane of the gasoline, and the LPG yield. However, the latter came at an expense of the gasoline yield loss.

The modification of MCM-56 by the selective cation exchange method and its incorporation in a RE-USY containing catalyst (Catalyst H) resulted in a reduction in the gasoline yield loss. Although the absolute gasoline octane gain was less than that observed for Catalyst G, the (ΔRON/ΔGasoline loss) ratio suggests that Catalyst H was more effective in increasing RON without a significant debit in gasoline yield. Table 5 shows that Catalyst G and H had (ΔRON/ ΔGasoline loss) ratios of 0.5 and 1.3, respectively. When "alumina-coated" MCM-56 was incorporated into a RE-USY containing catalyst (catalyst I), it offered similar benefits in the yield pattern of the cracked products to those of the catalyst containing the selective exchanged MCM-56 and RE-USY (catalyst H). Furthermore, the former yielded a higher octane gasoline than that of catalyst H, and had the highest combined gasoline and potential alkylate yield among the four catalysts at about 50% less MCM-56 than catalysts G and H.

Both catalysts H and I exhibited better bottom upgrading capabilities than catalysts F and G, as determined by the (Gasoline+LCO)/(HFO+Coke) ratios. Therefore, using modified MCM-56 in the catalytic cracking of petroleum feedstock should produce more high value liquid products, such as gasoline and distillate, and less bottoms fraction and coke.

We claim:

1. A layered composition of matter, MCM-56, which has an X-ray diffraction including the lines listed in Table II below:

TABLE II

| Interplanar d-Spacing (A) | Relative Intensity |
|---|---|
| 12.4 ± 0.2 | vs |
| 9.9 ± 0.3 | m–s |
| 6.9 ± 0.1 | w |
| 6.2 ± 0.1 | s |
| 3.55 ± 0.07 | m–s |
| 3.42 ± 0.07 | vs | and which has been selectively modified so that the ratio of the number of active acid sites at its external surface to the number of internal active acid sites is greater than that of the unmodified material.

2. The layered composition of matter of claim 1 which has been selectively modified so as to render the internal acid sites substantially catalytically inactive.

3. The layered composition of matter of claim 1 which has been selectively modified by the application of a coating of a catalytically active material to its external surface.

4. The layered composition of matter of claim 3 wherein the coating comprises an inorganic oxide material.

5. The layered composition of matter of claim 4 wherein the coating comprises alumina.

6. The layered composition of matter of claim 1 having a composition comprising the molar relationship $$X_2O_3:(n)YO_2,$$

wherein n is less than about 35, X is a trivalent element, and Y is a tetravalent element.

7. The layered composition of matter of claim 6 wherein n is from about 13 to about 18.

8. The layered composition of matter of claim 6 wherein X is a trivalent element selected from the group consisting of aluminum, boron, iron and gallium and Y is a tetravalent element selected from the group consisting of silicon and germanium.

9. The layered composition of matter of claim 6 wherein X is aluminum and Y is silicon.

10. A catalyst composition comprising a large pore zeolite cracking catalyst and a layered composition of matter, MCM-56, which has an X-ray diffraction including the lines listed in Table II below:

TABLE II

| Interplanar d-Spacing (A) | Relative Intensity |
|---|---|
| 12.4 ± 0.2 | vs |
| 9.9 ± 0.3 | m–s |
| 6.9 ± 0.1 | w |
| 6.2 ± 0.1 | s |
| 3.55 ± 0.07 | m–s |
| 3.42 ± 0.07 | vs | and which has been selectively modified so that the ratio of the number of active acid sites at its external surface to the number of internal active acid sites is greater than that of the unmodified material.

11. The catalyst composition of claim 10 wherein the layered composition of matter has been selectively modified so as to render the internal acid sites substantially catalytically inactive.

12. The catalyst composition of claim 10 wherein the layered composition of matter has been selectively modified by the application of a coating of a catalytically active material to its external surface.

13. The catalyst composition of claim 12 wherein the coating comprises alumina.

14. The catalyst composition of claim 10 wherein the layered composition has a composition comprising the molar relationship $X_2O_3:(n)YO_2$, wherein n is less than about 35, X is a trivalent element,and Y is a tetravalent element.

15. The catalyst composition of claim 14 wherein n is from about 13 to about 18.

16. The catalyst composition of claim 14 wherein X is aluminum and Y is silicon.

17. The catalyst composition of claim 10 wherein the large pore zeolite is a zeolite Y.

18. The catalyst composition of claim 10 comprising about 0.5 to 90% by weight of said layered composition of matter by weight of the catalyst composition.

19. A hydrocarbon conversion process comprising contacting a reaction stream comprising a hydrocarbon to be converted, under conversion conditions, with a layered composition of matter, MCM-56, which has an X-ray diffraction including the lines listed in Table II below:

TABLE II

| Interplanar d-Spacing (A) | Relative Intensity |
|---|---|
| 12.4 ± 0.2 | vs |
| 9.9 ± 0.3 | m–s |
| 6.9 ± 0.1 | w |
| 6.2 ± 0.1 | s |
| 3.55 ± 0.07 | m–s |
| 3.42 ± 0.07 | vs | and which has been selectively modified so that the ratio of the number of active acid sites at its external surface to the number of internal active acid sites is greater than that of the unmodified material.

20. The process of claim 19 selected from the group consisting of catalytic cracking of a heavy hydrocarbon feedstock, alkylation of an aromatic feedstock with an olefin, and alkylation of isoparaffin with an olefin.

* * * * *